United States Patent [19]

Trepte

[11] 4,233,516
[45] Nov. 11, 1980

[54] X-RAY IMAGE DETECTION APPARATUS

[75] Inventor: Wulf Trepte, Holmbodavägen, Sweden

[73] Assignee: Siemens Aktiengesellschaft, Berlin & Munich, Fed. Rep. of Germany

[21] Appl. No.: 942,667

[22] Filed: Sep. 15, 1978

Related U.S. Application Data

[63] Continuation of Ser. No. 745,557, Nov. 29, 1976, abandoned.

[30] Foreign Application Priority Data

Dec. 22, 1975 [DE] Fed. Rep. of Germany ....... 2557810

[51] Int. Cl.$^3$ .......................................... G03B 41/16
[52] U.S. Cl. ................................... 250/444; 250/521
[58] Field of Search ................. 250/468, 521, 439 R, 250/444, 445 R, 446, 447, 448, 449, 490, 523

[56] References Cited

U.S. PATENT DOCUMENTS 3,434,684  3/1969  Warden ............................... 250/521

FOREIGN PATENT DOCUMENTS 689324  3/1953  United Kingdom ................... 250/521

Primary Examiner—Craig E. Church
Attorney, Agent, or Firm—Hill, Van Santen, Steadman, Chiara & Simpson

[57] ABSTRACT

X-ray image detection apparatus in which an image detector is pivotally mounted on a carrier arm which in turn is pivotally mounted on a vertical column. A sprocket wheel and chain arrangement operatively interconnects the image detector, the carrier arm and the vertical column such that as the carrier arm is pivoted about a horizontal axis in one direction relative to the vertical column, the image detector is pivoted in an opposite direction.

1 Claim, 3 Drawing Figures

X-RAY IMAGE DETECTION APPARATUS

This is a continuation of application Ser. No. 745,557, filed Nov. 29, 1976, now abandoned.

BACKGROUND OF THE INVENTION

This invention relates generally to the field of X-ray equipment and more particularly to X-ray image detection apparatus having an image detector such as a film carrier movable between horizontal and vertical position for receiving radiation in either direction.

X-ray image detection apparatus of this general type may be found in the prior patented art. For example, U.S. Pat. No. 3,434,684, assigned to the assignee of the present application, discloses apparatus in which an X-ray image intensifier is pivotally mounted on a stand for receiving both horizontal and vertical radiation. The disclosed apparatus, while having substantial utility, suffers from certain deficiencies, however.

For example, when the disclosed apparatus is being used in conducting vertical radioscopy of a patient the entire apparatus must be placed under the table or bed on which the patient is being examined. This can be a source of difficulty and inconvenience to the physician. Then, in the course of the examination, the elevation of the apparatus must often times be varied, but in some situations the height of the examination table is not sufficient to accommodate all positions of the X-ray apparatus.

Furthermore, when the apparatus is thereafter repositioned to accommodate horizontal radioscopy, it is usually necessary to again adjust the height of the apparatus as a consequence of the thickness of the mattress or pad on the bed or examination table. Such variations in heighth are either unavailable or are accomplished only with great difficulty in previously known image detection apparatus.

It is, therefore, an object of the present invention to provide X-ray image detection apparatus in which only the actual image detector portion thereof need be located under the examination table during vertical radioscopy, the stand portion thereof being located on the side of the table.

Another object is to provide X-ray image detection apparatus in which the image detector portion is automatically raised as the detector is changed from a position to accommodate vertical radioscopy to a position to accommodate horizontal radioscopy.

SUMMARY OF THE INVENTION

The invention may be summarized as comprising a vertical stand or column upon which is mounted an image detector such as a film carrier. The image detector is mounted on the stand or column by means of a pivotal carrier arm and a vertically movable mounting block such that the image detector can be raised and lowered relative to the stand and can be located under the examination table while the column is located adjacent the table. In addition, a sprocket wheel and chain arrangement operatively interconnects the column, the carrier arm and the image detector, such that as the carrier arm is pivoted relative to the column, the image detector is also pivoted to accommodate vertical and horizontal radioscopy, and is simultaneously raised and lowered in accordance with the height requirements of the two directions of radioscopy.

Thus, in accordance with the principles of the present invention, the stand or column upon which the image detector is mounted is located adjacent the examination table, the image detector can be raised or lowered under the table, and then, when the image detector is pivoted from a horizontal to a vertical position, it is simultaneously and automatically elevated.

Many other features, advantages and additional objects of the present invention will become manifest to those versed in the art upon making reference to the detailed description which follows and the accompanying sheets of drawings, in which a preferred structural embodiment incorporating the principles of the present invention is shown by way of illustrative example only.

DESCRIPTION OF THE PREFERRED EMBODIMENT

Figure 1:
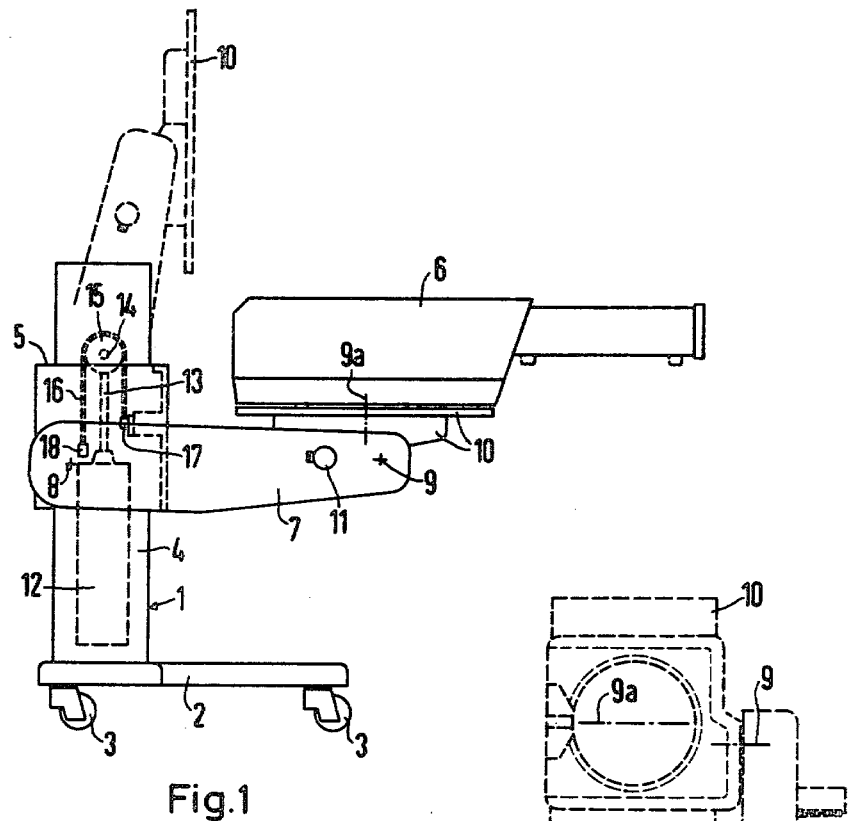
FIG. 1 is a side elevational view of X-ray image detection apparatus constructed in accordance with the principles of the present invention with portions thereof shown somewhat schematically.
Figure 2:
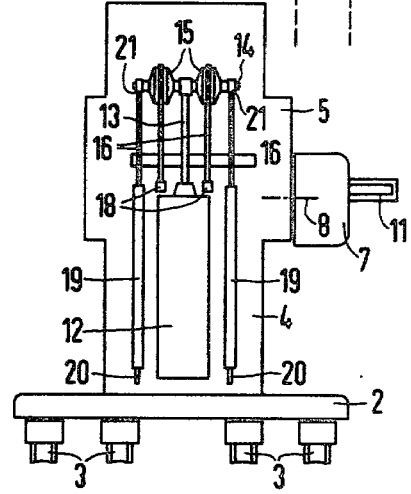
FIG. 2 is a rear elevational view of the apparatus shown in FIG. 1.

Referring to FIGS. 1 and 2, X-ray image detection apparatus constructed in accordance with the principles of the present invention is indicated generally at reference numeral 1, and includes a horizontal base or undercarriage 2 which is equipped with a plurality of rollers or wheels as indicated at reference numerals 3, so that the undercarriage can be easily moved about on a supporting floor surface such as the floor of an examination room.

A vertical column or stand 4 is mounted on the undercarriage 2, and carried for vertical movement thereon is a mounting block or adjustment mechanism indicated at 5. Vertical adjustment of the mounting block 5 effects vertical adjustment of an image detector, such as a film carrier indicated at 6, to which the mounting block 5 is operatively connected by means of an elongated carrier arm 7.

The carrier arm 7 is pivotally mounted on one side of the mounting block 5 by means of a horizontal axle or pivot pin, indicated diagrammatically at reference numeral 8, disposed adjacent one end of the carrier arm 7. The image detector 6 is pivotally mounted on the carrier arm 7 by means of a plate 10, to which the image detector 6 is removably connected, and a second horizontal axle or pivot pin, indicated diagrammatically at reference numeral 9, located adjacent the opposite end of the carrier arm 7.

Figure 3:
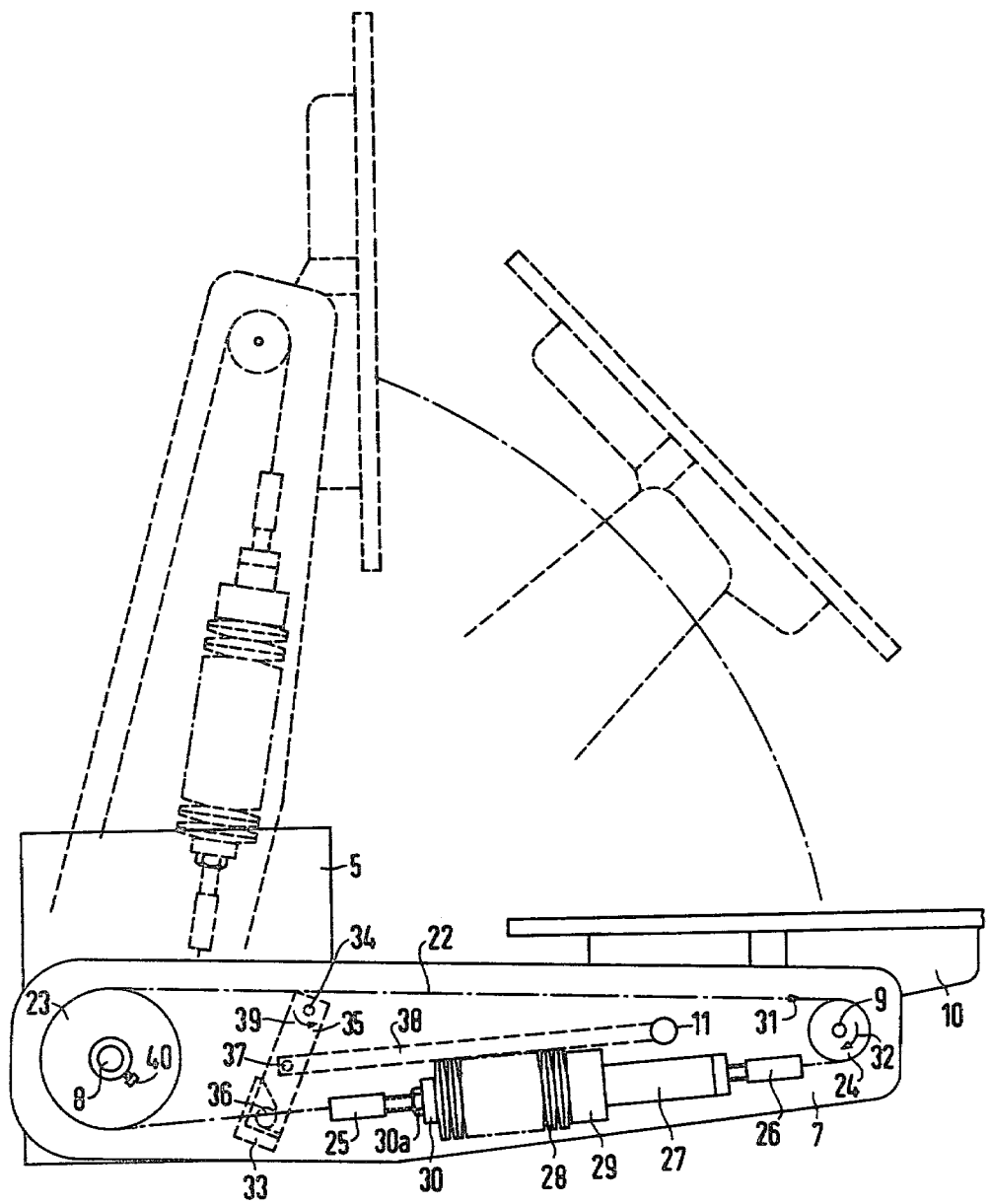
FIG. 3 is an enlarged side elevational view of the carrier arm portion of the apparatus.

Reference numeral $9_a$ indicates the central axis of the image detector 6, and as shown in FIG. 1, extends in a vertical direction when the image detector 6 is disposed for horizontal radioscopy, and as shown in FIG. 3, extends in a horizontal direction when the image detector 6 is disposed for vertical radioscopy.

The carrier arm 6 is equipped with a handle 11, by which it can be pivoted or swung manually from a substantially horizontal position as shown in the solid lines in FIGS. 1–3, to a substantially vertical position as shown in the dashed lines of FIGS. 1–3. It is noted that in FIGS. 1–3, the image detector 6 is not shown in dashed lines for the purpose of simplifying the drawings, but the plate 10 is shown, from which the position of the image detector 6 can be determined.

The mounting block 5 is adjusted vertically by means of a motor 12. The body of the motor 12 is fixed to the column 4, and projecting from the upper end of the motor 12, which may preferably be of the hydraulic or pneumatic type, is a vertically extensible rod 13. Mounted on the upper end of the rod 13 is a shaft 14, on which are rotatably mounted a pair of sheaves 15, 15. Trained about the sheaves 15, 15 are a pair of cables 16, one end of each of which, as shown at reference numeral 17, is connected fast or in fixed assembly to the mounting block 5, and an opposite end of each of which, as shown at reference numeral 18, is connected fast to the column 4. A pair of pneumatic springs 19 extend vertically on either side of the motor 12, and each has a lower end 20 connected fast to the column 4, and an upper end 21 rotatably connected to the shaft 14.

The mounting block 5, and thus the carrier arm 7, may be raised and lowered vertically by means of the motor 12. When the motor 12 is actuated in a manner whereby the rod 13 rises relative to the body of the motor 12, the shaft 14 also rises vertically since the ends 18 of the cables 16 are affixed to the column 4, the effect of the vertical upward movement of the shaft 14 is to cause the sheaves 15 to rotate, thereby causing an upward movement of the ends 17 of the cables 16, and thus the mounting block 5.

When the motor 12 is actuated in a manner whereby the rod 13 moves vertically downwardly, the downward movement of the shaft 14 effects rotation of the sheaves 15 in an opposite direction, and the ends 17 of the cables 16 as well as the mounting block 5 also move vertically downwardly. The pneumatic springs 19 perform the function of cushioning the movement of the mounting block 5 with respect to the stationary column 4.

In operation, the X-ray image detection apparatus 1 can be wheeled to a position adjacent the examination table, whereby the carrier arm 7 can be lowered sufficiently such that the image detector 6 can be moved under the horizontal portion of the examination table on which the patient rests. Vertical radioscopy can then be carried on where essentially only the image detector 6 under the examination table, the vertical column 4 being disposed alongside the table.

For carrying out horizontal radioscopy, the carrier arm 7 can be pivoted to the position thereof shown in dashed lines in FIGS. 1–3 by grasping the handle 11 and lifting the distal end of the carrier arm such that it swings or pivots in a counterclockwise direction in the view thereof shown in FIG. 1 until the arm 7 attains a substantially vertical position. As the carrier arm 7 is being pivoted counterclockwise, however, the image detector 6 is simultaneously and automatically being pivoted about the axis 9 in a counterclockwise direction, as indicated by the vertical disposition of the plate 10 in the position thereof shown in the dashed lines thereof in FIG. 1.

The simultaneous and automatic pivoting of the image detector 6 is effected by a sprocket wheel and chain arrangement, the details of which are shown in FIG. 3.

As shown in FIG. 3, a sprocket wheel 23 is mounted on the axle 8 about which the carrier arm 7 pivots relative to the mounting block 5. The axle or pivot pin 8 and the sprocket wheel 23 are both connected in fixed assembly to the carrier arm 7 such that neither rotates with respect to the carrier arm 7, but instead the axle 8 is journalled for rotation relative to the mounting block 5.

Another sprocket wheel 24 is mounted on the axle 9. In this instance, however, while the sprocket wheel 24 is mounted fast on the axle 9, the axle itself is journalled for rotation relative to the carrier arm 7, but is connected in fixed assembly to the plate 10 upon which the image detector 6 is mounted.

Trained around the sheaves 23 and 24 is a chain 22, one end of which is connected to a chain connector 25 and the other end of which is connected to a chain connector 26. Connector 26 is in turn connected to an elongated rod 27, around a portion of which is wrapped a coil spring 28. One end of the coil spring 28 bottoms on a spring abutment block 29 which is securely fastened to the carrier arm 7, while an opposite end of the coil spring 28 bottoms on a disc 30, which can be adjusted on the spring rod 27 by virtue of an adjustment nut $30_a$.

As a consequence of the coil spring 28, the spring rod 27 is constantly biased leftwardly in the view thereof shown in FIG. 3, and the degree of the bias can be adjusted by virtue of the nut $30_a$.

As the carrier arm 7 is pivoted in a counterclockwise direction as viewed in FIG. 3, from the intermediate position thereof to the full vertical position shown in the dashed lines in FIG. 3, the axle 8 and the sprocket wheel 23 rotate jointly with the carrier arm 7. As a consequence of this movement the chain 22 moves, relative to the sheave 23, in a direction shown by the arrowhead 31, and in doing so rotates the axle 9 and the sprocket wheel 24 in a direction shown by the arrowhead 32. This rotation of the axle 9 tends to rotate the plate 10, and thus the image detector 6, in a clockwise direction, as the carrier arm 7 is being pivoted in a counterclockwise direction.

Thus as the carrier arm 7 moves from the horizontal position thereof shown in the solid lines in FIG. 3, to the vertical position thereof shown in the dashed lines, the plate 10 and the image detector mounted thereon are both raised upwardly vertically, while simultaneously they are automatically pivoted or rotated in a clockwise direction. Thus by lifting or pivoting the carrier arm 7 to accommodate horizontal radioscopy, the image detector 6 is not only rotated 90° but is simultaneously raised. Since normally the image detector 6 must be raised, by virtue of the thickness of the mattress or pad on the examination table, this feature of the invention reduces the time necessary to adjust the apparatus 1 as it is used for both horizontal and vertical radioscopy.

The coil spring 28 performs the function of a counterbalance. Thus, when the carrier arm 7 is pivoted counterclockwise in the view thereof shown in FIG. 3, the tension in the coil spring 28 is reduced, thereby enabling the carrier arm 7 to be pivoted upwardly more easily. On the other hand, when the carrier arm 7 is rotated clockwise back to the position thereof shown in the solid lines in FIG. 3, the tension in the coil spring 28 increases, thereby serving as a counterweight to the carrier arm 7.

The position of the plate 10 (and the image detector 6) relative to the carrier arm 7 can be adjusted by virtue of a locking screw 40 mounted on the sprocket wheel 23. When the screw 40 is tightened, the sprocket wheel 23 and the axle 8 are locked together for joint movement. The screw 40 can be loosened, however, whereby the sprocket wheel can be rotated relative to the axle 8, and such rotation of the sprocket wheel 23 has the effect of rotating the plate 10 relative to the carrier arm 7. After the carrier plate 10 has been adjusted to a desired position relative to the carrier arm 7, the screw 40 can be once again tightened, thereby again locking the sprocket wheel 23 to the axle 8 to maintain the desired position of the plate 10 relative to the carrier arm 7.

The invention also contemplates the utilization of mechanical stops for limiting the pivotal movement of the carrier arm 7. As shown in FIG. 3, an arm or lever 35 is pivotally mounted on the mounting block 5 by virtue of a pivot pin 34. One end of an elongated rod 38 is connected to the lever 35 by means of a pivot pin 37, which is located in a position remote from the pivot pin 34.

Extending from the lever 35 is another pin 36 which, in the position thereof shown in FIG. 3, is in abutting engagement with an abutment bracket or stop 33 which is securely fastened to the mounting block 5.

It will be appreciated that as the carrier arm 7 is pivoted in a counterclockwise direction as viewed in FIG. 3, the lever 35 also pivots in a counterclockwise direction as shown by the arrowhead 39. This pivotal movement of the lever 35 moves the pin 36 out of engagement with the stop 33.

On the other hand, when the carrier arm 7 is pivoted in a clockwise direction as viewed in FIG. 3, the pin 36 will again abut the stop 33 to provide a physical limiting position of the carrier arm 7.

Another stop or abutment bracket similar to that indicated at reference numeral 33 may be mounted on the mounting block 5 in a suitable position to receive the pin 36 in abutment to provide a physically limiting position of the carrier arm 7 when the same is pivoted in a counterclockwise direction.

It should be understood that the principles of the present invention are applicable regardless of whether the apparatus 1 is used in conjunction with an image detector or film carrier 6, or an X-ray image amplifier or intensifier or other equipment of similar nature.

Although minor modifications might be suggested by those versed in the art, it should be understood that I wish to embody within the scope of the patent warranted hereon all such modifications as reasonably come within the scope of my contribution to the art.

I claim as my invention:

1. In x-ray image detection apparatus including a wheeled undercarriage, a vertical column supported by said undercarriage, a mounting block carried on said column for vertical movement relative thereto, an image detector mechanism having a radiation receiving side and means for mounting said image detector mechanism on said mounting block, an improvement wherein: said mounting means comprises an elongated carrier arm with first and second ends, first pivot means for connecting said first end of said carrier arm to said mounting block for pivotal movement of said carrier arm about a horizontal axis between horizontal and substantially vertical positions, second pivot means for mounting said image detector mechanism on said second end of said carrier arm for pivotal movement of said image detector mechanism about a horizontal axis between horizontal and vertical positions, and means interconnecting said first and second pivot means for effecting first and second pivotal movements of said image detector mechanism from a horizontal position, with the radiation receiving side oriented upwardly to receive vertically, downwardly directed radiation, and with the carrier arm in a horizontal position, to a vertical position, with the radiation receiving side oriented vertically and away from the vertical column to receive horizontally directed radiation, and with the carrier arm in a substantially vertical position behind the image detection apparatus; during said first pivotal movement, said image detector mechanism rotates essentially ninety degrees in a first rotational direction and moves upwardly simultaneously while said carrier arm rotates upwardly through an angle of no more than ninety degrees in a direction opposite said first rotational direction, during said second pivotal movement, said image detector mechanism rotates essentially ninety degrees in a direction opposite said first rotational direction and moves downwardly simultaneously while said carrier arm rotates downwardly through said angle in said first rotational direction.

* * * * *